United States Patent [19]

Drake et al.

[11] Patent Number: 4,952,177
[45] Date of Patent: Aug. 28, 1990

[54] CLAMP FOR ELECTRO-SURGICAL DISPERSIVE ELECTRODE

[75] Inventors: Gerald E. Drake, St. Paul, Minn.; Robert L. Goodlad, Star Prairie, Wis.; William K. Weimer, St. Louis Park, Minn.

[73] Assignee: Minnesota Mining and Manufacturing Company, St. Paul, Minn.

[21] Appl. No.: 452,720

[22] Filed: Dec. 19, 1989

[51] Int. Cl.⁵ .............................................. H01R 9/07
[52] U.S. Cl. .................................................... 439/828
[58] Field of Search ............... 439/217, 218, 170, 171, 439/172, 174, 725, 838

[56] References Cited

U.S. PATENT DOCUMENTS

| | | |
|---|---|---|
| 3,842,394 | 10/1974 | Bolduc . |
| 4,023,879 | 5/1977 | Braund et al. ....................... 439/172 |
| 4,061,408 | 12/1977 | Bast et al. . |
| 4,416,276 | 11/1983 | Newton et al. . |
| 4,555,155 | 11/1985 | Drake ..................................... 439/838 |
| 4,738,263 | 4/1988 | Seebach et al. . |
| 4,761,143 | 8/1988 | Owens et al. ........................ 439/372 |
| 4,768,969 | 9/1988 | Bauer et al. .......................... 439/372 |
| 4,873,973 | 10/1989 | Hagen et al. ......................... 439/838 |

FOREIGN PATENT DOCUMENTS 2091955  8/1982  United Kingdom ................ 439/418

OTHER PUBLICATIONS

Sebben, J. E., "Patient 'Grounding'", J. Dermatol. Surg. Oncol. 14:9, 926–931 (1988).

Primary Examiner—Joseph H. McGlynn
Assistant Examiner—Hien D. Vu
Attorney, Agent, or Firm—Donald M. Sell; Walter N. Kirn; John H. Hornickel

[57] ABSTRACT

A clamp for releasably engaging dispersive electrodes is disclosed. The clamp is adaptable to be used either with electro-surgical generating equipment which has a unitary plate continuity safety circuit or with an electro-surgical generating equipment which has an impedance split-plate impedance safety circuit. The clamp electrically adapts a split-plate electrode to be useful with an electro-surgical generating equipment which has a unitary plate continuity safety circuit.

11 Claims, 3 Drawing Sheets

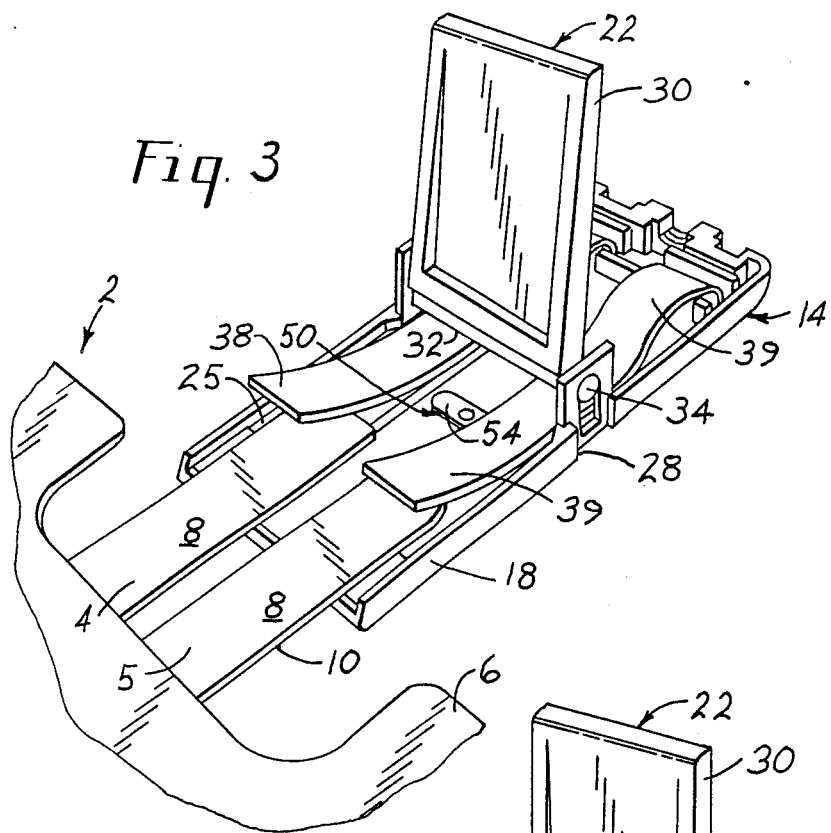

CLAMP FOR ELECTRO-SURGICAL DISPERSIVE ELECTRODE

FIELD OF THE INVENTION

This invention relates to a clamp for a dispersive electrode adaptable for use with different types of electro-surgical generating equipment.

BACKGROUND OF THE INVENTION

In recent years, electro-surgery has become a more useful tool for surgeons to operate on patients replacing the surgical metal scalpel with an electro-surgical cutting electrode.

An electro-surgical system usually comprises a generator providing high-frequency alternating current on demand under monitored conditions, the cutting electrode having an extremely high-current density and a flat dispersive electrode having a very large surface area to provide a low-current density. The utility of providing a dispersive electrode has been described in the literature, for example, in J. Dermatol. Surg. Oncol. 1988; 14:926-931.

The dispersive electrode of the alternating current electro-surgical system is placed in intimate and continuous contact with a portion of the body of the patient which is not subject to the surgical procedure. The alternating current circuit is completed through the body of the patient between the dispersive electrode and the cutting electrode. Disconnection of the dispersive electrode either from contacting the patient or from the generator could subject the patient to electrical burns where the alternating current circuit leaves the body of the patient. The electrical burns could be nearly as intense as the electrical incision.

Generally, electro-surgery generators include a safety disconnect circuit to prevent skin burns if the dispersive electrode fails to maintain a proper, dispersing electrical connection between the generator and the body of the patient. One type of electro-surgery generating equipment has a continuity testing safety circuit requiring the use of a unitary plate dispersive electrode. Another type of electro-surgery generating equipment has an impedance safety circuit requiring the use of a split-plate dispersive electrode.

For example, U.S. Pat. No. 4,416,276 describes a generating system which has a return electrode impedance monitoring safety circuit using a split-plate dispersive electrode.

Hence, with at least two known types of systems of electro-surgical generators, two types of dispersive electrodes, unitary plate electrodes and split-plate electrodes, have been developed in the industry specifically for their respective generating systems. When a hospital or other surgical arena uses both types of electro-surgical generating systems, it is necessary to maintain a supply of each type of dispersive electrode, because heretofore, each type of electrode is specifically adapted for use with a particular type of electro-surgical generating system. Misuse or incorrect selection of the proper type of dispersive electrode with the proper system can occur when multiple types of electrodes must be kept in inventory.

For each electro-surgical generator system, a connector device must be provided for connecting the appropriate dispersive electrode to the generator system. Because of the variety of electrode types, a variety of connector devices have also been developed to establish electrical connection between the generator and the body of the patient. For example, in U.S. Pat. No. 4,738,263, which involves a unitary dispersive electrode, a connector having a pair of leads is disclosed to engage a pair of engagement holes on the electrode. Another example is that disclosed in U.S. Pat. No. 3,842,394 also involving a unitary dispersive electrode, where a spring-biased connector clamps to the surface of the electrode plate.

Lever actuated clamps are disclosed in U.S. Pat. Nos. 4,061,408 and 4,768,969 which show single-plate electrodes being secured by the lever actuated pressure within the connectors.

The problem in the art is that a specific type of dispersive electrode has been developed for each type of electro-surgical generating system requiring the maintenance of separate inventory of electrodes for each system. The connector devices known have provided no facility which would permit one type of electrode to be useful with the type of generating system for which it was developed and also to be electrically adapted to be useful with the other type of generating system.

What is needed in the art is a clamp which can be connected to either electro-surgical generators which require unitary dispersive electrodes or electro-surgical generators which required split-plate dispersive electrodes. By providing the clamp with an electrical contact configuration which electrically adapts one type of electrode into another type of electrode, a single type of dispersive electrode may be used with electro-surgical generating equipment of various types.

SUMMARY OF THE INVENTION

This invention provides a solution to the problems encountered in the electro-surgical generating art by providing a clamp which is useful with both types of electro-surgical generating systems.

It is an object of the invention to provide a clamp which may releasably engage a split-plate electrode having split tabs or a unitary plate electrode having a single tab.

It is another object of the invention to provide a clamp of the present invention which electrically adapts a split-plate dispersive electrode to serve either an electro-surgical generating system having an impedance split safety circuit or an electro-surgical generating system having a unitary continuity safety circuit.

It is another object of the invention to provide a clamp which has two separated electrical contact strips for contacting the split tabs of the electrode and a third bridge electrical contact strip between the separated strips. Depending upon the orientation of the split-plate dispersive electrode's tabs being releasably inserted into the clamp, the bridging contact may cause the split-plate dispersive electrode to function as a unitary dispersive electrode or a split-plate dispersive electrode.

Generally, the present invention provides a connector for releasably engaging an electrically useful device, such as an electrode, which has plurality of projecting tabs separated from one another and having opposed electrically conductive and insulated surfaces. This connector includes a housing having an exterior surface, an interior surface being formed within said housing for receiving the projecting tabs, and a slot disposed in said housing between the exterior surface and the interior surface. Located on the interior surface, there exists a plurality of receiving means separated from one another, each means for electrically contacting a corresponding electrically conductive surface on the separately projecting tabs. Disposed on the interior surface, there exists bridging means for electrically contacting the plurality of receiving means whenever a plurality of electrically conductive surfaces of the projecting tabs contacting the corresponding plurality of separated means also contact the bridging means. The invention is described in greater detail with reference to the drawings and a description of the embodiments of the invention.

BRIEF DESCRIPTION OF DRAWINGS

FIG. 3 is a depiction of an alternate embodiment of the present invention adapted for use in one mode of operation. For purposes of clarity, the upper cover of the clamp has been removed.

FIG. 4 is the alternate embodiment of FIG. 3 illustrating use in its second mode of operation. Again, the upper cover has been removed for clarity.

EMBODIMENTS OF THE INVENTION

Figure 1:
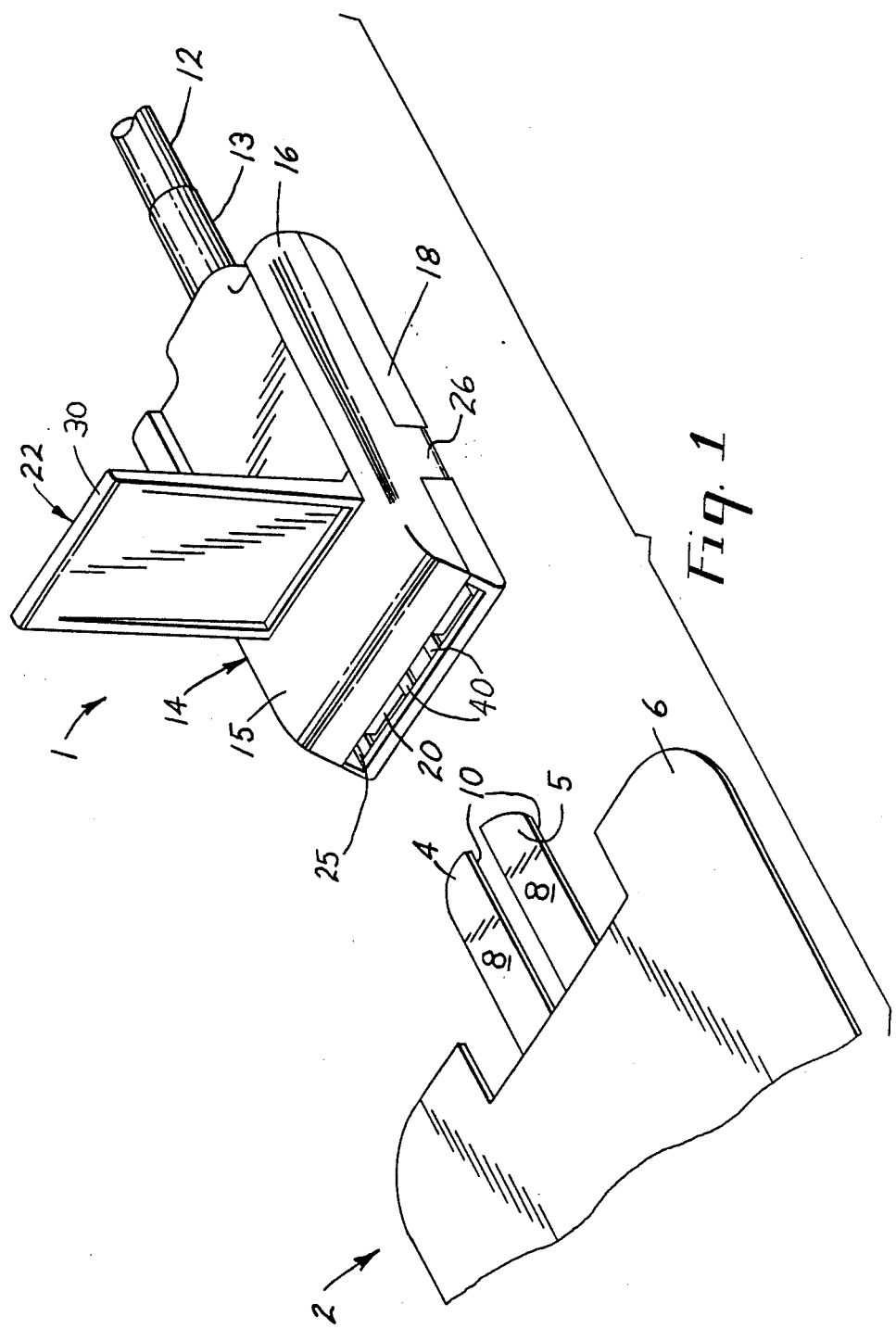
FIG. 1 is a perspective view of a clamp according to the present invention along with a portion of a split-plate dispersive electrode known in the art, particularly showing the pluralitY of the projecting tabs of the electrode having opposing conductive and insulated surfaces.

Referring to FIG. 1, an understanding of the versatility of one preferred embodiment of the clamp of the present invention may be understood. The clamp 1 is shown engaging the split-plate dispersive electrode 2 as a portion of the electro-surgical generating system (not shown).

The split-plate dispersive electrode 2 has two separate tabs, 4 and 5, projecting from a backing 6 of the electrode 2. Tabs 4 and 5 have opposed surfaces. One surface is an insulated surface 8 shown in FIG. 1 as the upper surface on both tabs 4 and 5. The opposing surface is a conductive surface 10, shown in FIG. 1 as the opposed under surface of tabs 4 and 5.

The clamp 1 is also useful with a unitary plate electrode which has an undivided projecting tab, typically having an insulative surface and a conductive surface. Further, the clamp 1 may be used with any other electrically useful device having a terminal for electrical contact with another electrically useful device.

The clamp 1 is connected to a cable 12 having a strain relief 13 engaging a clamp housing 14 having an exterior surface 15. The cable 12 is connected to the electro-surgical generator (not shown) which may require an electrical adaptor for proper electrical connection.

The housing 14 is divided into a first cover 16 and a second cover 18. The housing 14 is configured to have a tabs receiving slot 20 at a point on its exterior surface 15 of joinder between first cover 16 and second cover 18 to allow insertion of the tabs 4 into the housing 14.

A lever 22 in communication with interior surfaces 25 of the housing 14 extends through a lever slot 24 on the exterior surface 15 of the first cover 16.

Figure 2:
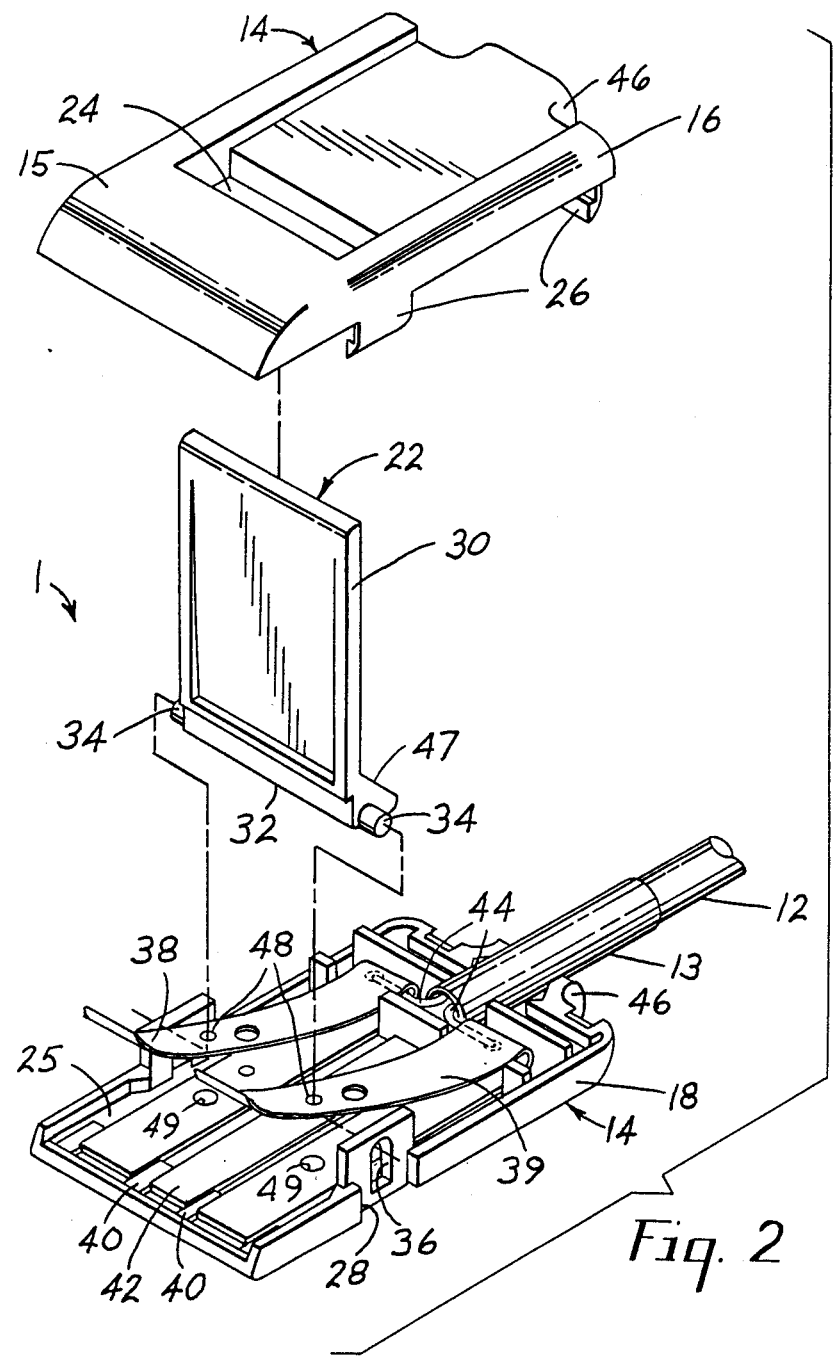
FIG. 2 is an exploded view of the clamp of the present invention as depicted in FIG. 1 revealing structure of the interior surface of the clamp.

Referring to FIG. 2, the first cover 16 and the second cover 18 are secured by latches 26 received in notches 28 in the housing 14 on exterior surface 15 not adjacent to the tabs receiving slot 20.

The lever 22 is composed of a handle 30, a pivot portion 32, from which extend oppositely disposed pins 34. Pins 34 reside in complimentary grooves 36 on the second cover 18 of the housing 14.

On the interior surface 25 of housing 14, two receiving electrical contact strips 38 and 39 are shown in their restrained positions separated from one another within second cover 18 as held laterally in place by fingers 40. In this embodiment, strips 38 and 39 are generally U-shaped flat springs configured to receive tabs 4 and 5, respectively.

Disposed laterally between the separated electrical contact strips 38 and 39 is a bridge electrical contacting strip 42 also held laterally in place by fingers 40. Wires 44 from lead cable 12 and strain relief 13 pass through a collar 46 on second cover 18 and are secured by soldering or other electrically conductive securing means to the respective separated electrical contact strips 38 and 39.

Referring again to FIG. 1, tabs 4 and 5 may be inserted through tabs receiving slot 20. As seen in FIG. 2, tab 4 contacts strip 38 and tab 5 contacts strip 39. Further, due to the relative dimensions of the widths of the tabs 4 and 5 compared with the widths of the contact strips 38 and 39 and the bridge electrical contact strip 42, portions of the tabs 4 and 5 also contact the bridge electrical contacting strip 42.

When tabs 4 and 5 are inserted into clamp 1 through slot 20, the tabs must be releasably engaged to maintain continuous electrical connection with the separated electrical contact strips 38 and 39. The means for releasably engaging the tabs 4 are composed of the lever 22 having the handle 30, pins 34 on pivot portion 32 and rotating in grooves 36, all previously described. The means further include a cam ridge 47, and desirably, projections 48 on one portion of U-shaped strips 38 and 39 mating with depressions 49 on an opposed portion of U-shaped strips 38 and 39.

When the exploded view of FIG. 2 is reassembled as shown in FIG. 1, rotation of the handle about pins 34 in notches 36 causes the pivot portion 32 in slot 24 to rotate cam 47 to engage the upper portions of the strips 38 and 39 into releasable engagement with tabs 4 and 5. Desirably, the pressure of projections 48 against tabs 4 and 5 causes a pressuring embossment of the strips 38 and 39 about tabs 4 and 5, respectively, mating in depressions 49.

Depending whether the insulated surface 8 or the conductive surface 10 of the tabs 4 and 5 contact the bridge electrical contacting strip 42, different results are achieved.

If the clamp 1 is connected to an electro-surgical generating system which has a continuity testing safety circuit which monitors a unitary dispersive electrode, insertion of the tabs 4 and 5 into the tabs receiving slot 20 with the insulated surface 8 disposed upwardly as shown in FIG. 1 will cause the conductive surfaces 10 of the tabs 4 and 5 to contact both separated electrical contact strips 38 and 39, respectively, adjacent the interior surface 25 of second cover 18 and the conductive surfaces 10 of tabs 4 and 5 will also contact the bridge electrical contacting strip 42. Contact of the bridge strip 42 by both conductive surfaces 10 of tabs 4 and 5 electrically connects the separated electrical contact strips 38 and 39 providing a unitary electrical current through wires 44 and lead wire 12 to the electro-surgical generating system. Strips 38 and 39 are effectively joined electrically. An electro-surgical generator with a unitary plate continuity safety circuit is effectively connected to a unitary plate electrode by clamp 1 which adapts a split-plate electrode to be useful as a unitary plate electrode.

In the event that the tabs 4 and 5 are inserted into slot 20 with insulating surfaces 8 oriented in the opposite manner shown in FIG. 1, i.e., downwardly, the clamp 1 functions electrically entirely differently. The conductive surfaces 10 of tabs 4 and 5 contact the portions of the U-shaped separated electrical contact strips 39 and 38, respectively, directed away from the interior surface 25 of second cover 18 while the opposed insulated surfaces 8 of tabs 4 and 5 contact bridge electrical contacting strip 42 and the other portions of strips 39 and 38, respectively, restrained on the interior surface 25 of cover 18. In this orientation, strip 42 is effectively insulated from strips 38 and 39. Two separate electrical currents are sent through each of the wires 44 from the separated electrical contact strips 38 and 39. Strips 38 and 39 remain separated electrically. An electro-surgical generator with a split-plate impedance safety circuit is thereby connected to a split-plate electrode through clamp 1.

Depending on the orientation of the electrode-clamp engagement, the clamp 1 of the present invention permits the use of a single type of split-plate dispersive electrode 2 with either an electro-surgical generating system requiring a unitary current or an electro-surgical generating system requiring a plurality of currents.

In the event that the split-plate dispersive electrode 2 is composed of more than two tabs 4 and 5, it is within the scope of the present invention to expand the clamp 1 to include additional separated electrical contacting strip(s) laterally separated from strips 38 and 39 and having additional bridge electrical contacting strip(s) disposed therebetween. Thus, for the plurality of tabs 4, 5 et al. on the electrode 2, there is a matching plurality of contact strips 38, 39 et al. within housing 14 and a bridge electrical contacting strip 42 et al. separating every two electrical contact strips.

The size and shape of the contact strips 38 and 39 are so configured as to avoid electrically contacting more than one of the projecting tabs 4 or 5. In other words, each tab 4 or 5 contacts only one electrical contact strip 38 or 39 and one bridge electrical contacting strip 42. To that extent, the plurality of tabs 4 and 5 on electrode 2 releasably engage a matching plurality of separated electrical contact strips 38 and 39. Depending upon the orientation of tabs 4 and 5 when inserted through slot 20 in clamp 1, the bridge electrical contacting strip 42 may contact the insulated surface 8 of each tab 4 or the conductive surface 10 of each tab 4. As stated above, different electrical results are achieved either way.

FIGS. 3 and 4 illustrate an alternative embodiment to the present invention. As seen in FIG. 3, the bridging contact strip 50 has a shorter length than strip 42 of the embodiment seen in FIG. 2. Strip 50 remains disposed on the interior surface 25 between strips 38 and 39 but is movable, desirably rotatable through second cover 18 and restrained by a detent (not shown) on the exterior surface 15 of second cover 18. As seen in FIG. 3, the bridge electrical contacting strip 50 is oriented such that its opposing ends 54 are perpendicular to but not in electrical contact with strips 38 and 39. As seen in FIG. 4, opposing ends 54 are oriented parallel with and not in electrical contact with strips 38 and 39.

Although strip 50 is shown in FIGS. 3 and 4 to be generally rectangularly shaped, it is understood that strip 50 may be of any shape which upon some movement of the strip 50 causes electrical contact of at least one of strips 38 and 39 to be lost.

When the split-plate dispersive electrode 2 is oriented as shown in FIG. 1 and FIG. 3, insertion of the tabs 4 and 5 through slot 20 allows conductive surfaces 10 on tabs 4 and 5 to contact the portions of strips 38 and 39 laterally restrained on the interior surface 25 of second cover 18. As bridge contacting strip 50 is oriented in FIG. 3, conductive surfaces 10 of tabs 4 and 5 as tabs 4 and 5 inserted into the clamp 1 contact the opposing ends 54 of strip 50. In other words, the bridging strip 50 is of sufficient length such that when rotated perpendicular to the path of electrode 2 insertion, the opposing ends 54 bridge the gap between tabs 4 and 5 and contact conductive surfaces 10. In the orientation shown in FIG. 3, the split-plate dispersive electrode 2 sends a current as if it were a unitary plate electrode to the electro-surgical generating system having a unitary plate continuity safety circuit.

The opposite result occurs when the strip 50 is oriented in the manner shown in FIG. 4, i.e., opposing ends 54 of strip 50 are parallel with the direction of the electrode 2 insertion into clamp 1. In this orientation, the strip 50 is unable to electrically contact either or both of the conductive surfaces 10 of tabs 4 and 5. In this orientation, the split-plate dispersive electrode 2 sends two separate currents to the electro-surgical generator having a split-plate impedance safety circuit.

When employing the embodiments shown in FIGS. 3 and 4, it should be noted that it is unnecessary to alter the orientation of insertion of the tabs 4 of electrode 2 into clamp 1 Rather, the orientation of the rotatable bridge electrical contact strip 50 determines the result.

As stated above, the clamp 1 is also useful to connect a unitary plate electrode to an electro-surgical generator having a continuity testing safety circuit. In this instance, the orientation of the electrode-clamp engagement does not produce different results as found when the clamp 1 is used with split-plate electrode 2. Because both strips 38 and 39 receive the same electrical signal from the undivided tab of a unitary plate electrode, the electrical contact through the bridging means 42 is redundant. However, because one clamp can be used with either type of electro-surgical generating system and either type of electrode, other connecting devices become unnecessary regardless of which system(s) a health care facility may use.

If it should occur that clamp 1 is attempted to be placed between incompatible electrodes and generators, the appropriate alarm on the generator would sound. Thus, clamp 1 is versatile to the extent of proper usage. Table 1 describes the various combinations using clamp 1 of the present invention with known generator types and the results therefrom.

TABLE 1

|   | Electrode | Orientation of Clamp | Generator Type | Result |
|---|---|---|---|---|
| 1. | Unitary | Adapt to Unitary | Continuity | Useful |
| 2. | Unitary | Adapt to Unitary | Impedance | Alarm |
| 3. | Unitary | Adapt to Split | Continuity | Useful |
| 4. | Unitary | Adapt to Split | Impedance | Alarm |
| 5. | Split | Adapt to Split | Impedance | Useful |
| 6. | Split | Adapt to Unitary | Continuity | Alarm |
| 7. | Split | Adapt to Split | Continuity | Depends on Machine |
| 8. | Split | Adapt to Unitary | Continuity | Useful |

While the clamp 1 is useful with unitary plate electrodes and continuity safety circuit generators regardless of orientation (Combination 1 and 3), clamp 1 is even more useful in Combinations 5 and 8 where a split-plate electrode may be useful with an impedance or a continuity safety generator, depending on the orientation of releasable engagement of clamp 1 with electrode 2. The remaining combinations, previously incompatible in the art, remain incompatible and undesirable, with the exception of Combination 7 which can depend on the safety circuitry of the particular electrosurgical generator.

As seen by reference to the embodiments disclosed herein and FIGS. 1–4, a variety of orientations of electrical connection may be achieved using one of the embodiments of the clamp of the present invention.

Regardless of the electrical connection during releasable engagement of electrode 2 in clamp 1, the clamp 1 may release the dispersive electrode 2 by lifting of handle 30 and pulling the clamp 1 from electrode 2. Strain relief 13 is desirably provided to eliminate strain on the cable 12 as wires 44 are electrically secured to strips 38 and 39. In this manner, clamp 1 may be re-used even if electrode 2 is disposed. However, during the releasable engagement of the electrode 2, electrical connection is firmly established to assure continuing dispersive current functions of the electrode 2 during the surgical procedure.

The clamp 1 of the present invention may be made from materials well known and used as housings for connections of electrical apparatus. For example, housing 14 including first cover 16, second cover 18, lever 22, and strain relief 13, may be made from polymeric materials or other non-conductive sturdy materials which insulate the clamp 1 from any current passing through electrode 2 and within insulated cable 12. For example, first cover 16, second cover 18, and lever 22 may be made of polypropylene having dispersed therein approximately 30 percent by weight of glass fibers.

The method of making first cover 16, second cover 18, and lever 22 is similar to manufacture of other electrical connector housings in a variety of electrical arts, including the use of injection molding using a die or dies having sufficient tooling tolerances to permit a snug fit of the various covers 16 and 18, and lever 22 rotatable therethrough.

Strips 38, 39 and 42 or 50 must be electrically conductive to facilitate the flow of current within the housing 14 as contemplated by the present invention in its various orientations from the electrode to the electro-surgical generator. Conductive metals such as copper and alloys of copper are desirable with nickel plated alloys of copper being particularly desirable. Use of half-hard beryllium copper prepared with nickel plating is preferred.

Other embodiments will be apparent to those skilled in the art from a consideration of this specification and the practice of the invention disclosed herein. It is intended that the specification and the description of the structure and materials employed be considered as exemplary only, with the true scope and spirit of the invention being indicated by the following claims.

What is claimed is:

1. A connector for releasably engaging a plurality of projecting tabs separated from one another and having opposed electrically conductive and insulated surfaces, comprising:
   (a) a housing having an exterior surface, an interior surface being formed within said housing for receiving the projecting tabs, and a slot in said housing disposed between said exterior surface and said interior surface,
   (b) a plurality of receiving means separated from one another and located on said interior surface, each receiving means for electrically contacting an electrically conductive surface on a corresponding projecting tab, and
   (c) bridging means disposed on said interior surface for electrically contacting said plurality of receiving means whenever a plurality of electrically conductive surfaces of the projecting tabs contacting said corresponding plurality of receiving means also contact said bridging means.

2. A connector according to claim 1, wherein said plurality of receiving means comprises two electrical contact strips laterally separated on said interior surface, and wherein said bridging means comprises a third electrical contact strip separate from but disposed between said two electrical contact strips, whereby whenever each conductive surface of the two projecting tabs contacts both said third electrical contact strip and one of said two electrical contact strips, said two electrical contact strips are electrically connected.

3. A connector according to claim 1, wherein said bridging means is moveable on said interior surface to contact the electrically conductive surfaces of the plurality of projecting tabs.

4. A connector according to claim 1, wherein each of the plurality of receiving means is electrically connected to an electro-surgical generating system having a safety disconnect circuit.

5. A connector according to claim 1, wherein whenever the plurality of projecting tabs are inserted through said slot and received at said interior surface, said plurality of receiving means contact both the electrical conductive surfaces and the electrical insulated surfaces of the projecting tabs and said bridging means contacts only one of the opposed surfaces of the projecting tabs.

6. A connector according to claim 5, wherein said housing further comprises means for releasably engaging the tabs at said interior surface in contact with said plurality of receiving means and said bridging means.

7. A connector according to claim 5, wherein when said bridging means contacts the electrically insulated surfaces of the plurality of the projecting tabs, said receiving means remain electrically unconnected.

8. A connector according to claim 5, wherein when said bridging means contacts the electrically conductive surfaces of the plurality of the projecting tabs, said receiving means are electrically connected.

9. A connector according to claim 1, wherein said bridging means is moveable on said interior surface to avoid contact with at least one of the electrically conductive surfaces of the plurality of projecting tabs.

10. A connector according to claim 9, wherein said bridging means rotates on said interior surface between two of said receiving means.

11. A clamp to electrically adapt a split-plate dispersive electrode having at least two electrically conductive surfaces extending therefrom into a unitary plate dispersive electrode, comprising:
   at least a pair of separately disposed and laterally spaced electrical contact strips;
   at least one separately disposed bridge electrical contact strip laterally spaced between said pair of contact strips;
   whereby said pair of contact strips are electrically connected when the electrically conductive surfaces of the split-plate electrode contact said bridge contact strip and each of electrically conductive surfaces also contacts one of said contact strips.

* * * * *